United States Patent [19]

Fox

[11] 4,014,255
[45] Mar. 29, 1977

[54] APPARATUS FOR USE IN DETERMINING THE CHARACTER OF FINELY DIVIDED OR PARTICULATE SOLID MATERIAL

[75] Inventor: Edward James Fox, Derby, England

[73] Assignee: Coal Industry (Patents) Limited, London, England

[22] Filed: Nov. 19, 1974

[21] Appl. No.: 525,200

[30] Foreign Application Priority Data

Dec. 14, 1973 United Kingdom ............ 58022/73

[52] U.S. Cl. .................................. 100/99; 100/152
[51] Int. Cl.² ........................................ B30B 15/00
[58] Field of Search ......... 198/47, 53 R, 54, 56–58, 198/40, 204, 206, 207, 39, 540, 546, 502; 100/99, 151, 152, 119; 250/272, 277 R, 358 R, 453, 492 R, 308, 359, 360; 73/32 R; 209/79, 111.5

[56] References Cited

UNITED STATES PATENTS

| | | | |
|---|---|---|---|
| 1,235,406 | 7/1917 | Williams | 198/204 |
| 2,275,780 | 3/1942 | Maloney | 100/151 |
| 2,324,869 | 7/1943 | Oman | 100/151 |
| 3,052,353 | 9/1962 | Pritchett | 209/111.5 |
| 3,539,316 | 11/1970 | Trethewey | 198/39 |
| 3,678,268 | 7/1972 | Reim et al. | 250/354 |
| 3,710,104 | 1/1973 | Pavlik | 250/272 |
| 3,722,676 | 3/1973 | Mathews | 209/111.5 |
| 3,828,919 | 8/1974 | Holtsclaw et al. | 198/204 |

Primary Examiner—Evon C. Blunk
Assistant Examiner—Joseph E. Valenza
Attorney, Agent, or Firm—Stevens, Davis, Miller & Mosher

[57] ABSTRACT

Material to be presented to a beam of electro-magnetic radiation to determine a characteristic of the material, for example, the ash content of the material is conveyed as a bed along a flat conveying deck. The initial boundaries of the bed of material are determined by an inverted trough shaped guide of uniform cross-sectional area. The material is then compacted by an extension of the inverted trough shaped guide, the extension being of tapering cross-sectional area.

7 Claims, 3 Drawing Figures

APPARATUS FOR USE IN DETERMINING THE CHARACTER OF FINELY DIVIDED OR PARTICULATE SOLID MATERIAL

This invention relates to apparatus for use in determining the character of finely divided or particulate solid material and in particular the present invention provides apparatus for presenting finely divided or particulate solid material to a beam of electro-magnetic radiation, for example X or gamma radiation for the purpose of determining some characteristic of the material, for example, the ash content of a coal sample by measuring the amount of radiation back-scattered by the material.

In using irradiating beams for sampling purposes it is desirable to irradiate a substantial sample of material in order that a reliable average value of the particular characteristic, for example, ash content in the case of a coal sample, may be obtained.

An object of the present invention is to provide an improved apparatus for presenting sample material to an irradiating beam.

According to the present invention, apparatus for presenting finely divided or particulate solid material to a beam of electro-magnetic radiation to determine a characteristic of the material, comprises a linear conveyor having a flat material conveying surface, a delivery station for delivering material onto the conveying surface, a guide assembly on the downstream side of the delivery station for defining the boundaries of a bed of material on the conveying surface and for compacting the bed of material.

Preferably, the guide assembly comprises an inverted trough shaped guide.

Preferably, the guide assembly includes an extension of the inverted trough shaped guide, in use compaction of the bed of material being achieved by reducing the area of cross-section of the inverted trough shaped guide.

Advantageously, said extension of the inverted trough shaped guide includes inclined material guides.

By way of example only, one embodiment of the present invention will be described with reference to the accompanying drawings, in which.

Figure 1:
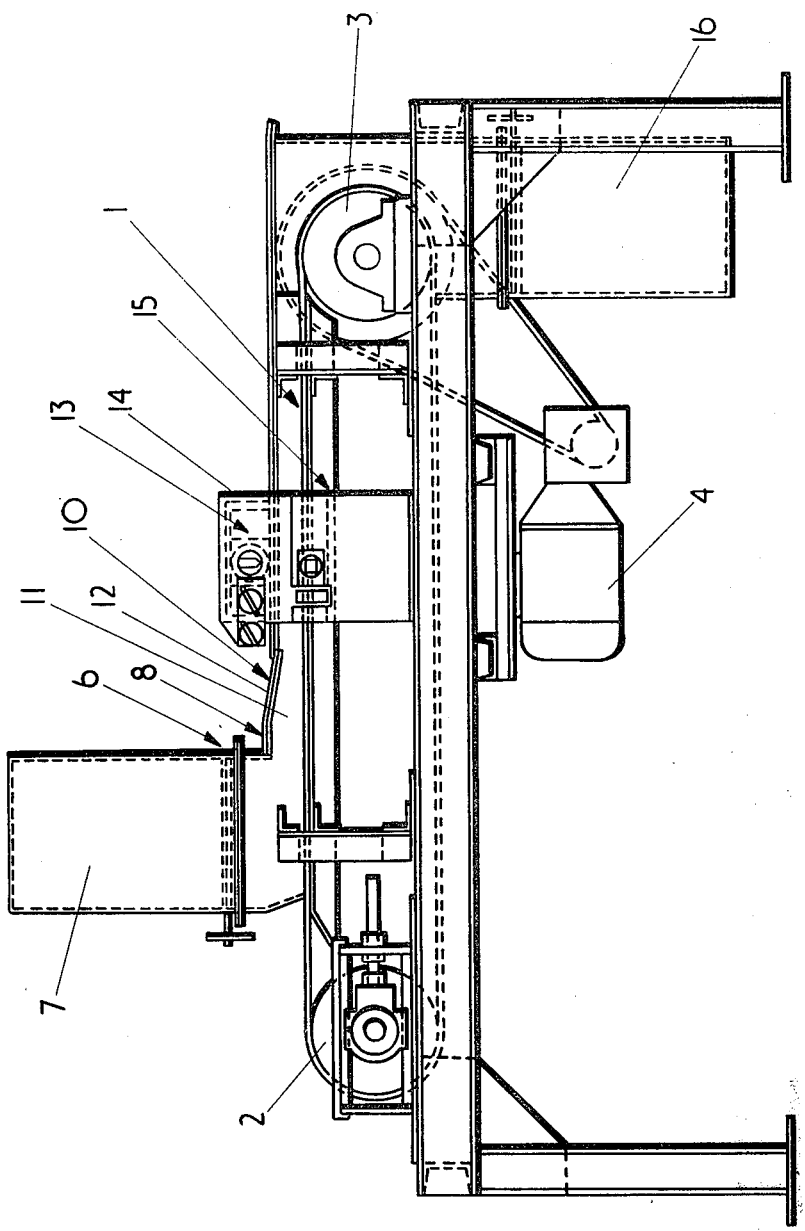
FIG. 1 is a side view of apparatus constructed in accordance with the present invention.
Figure 2:
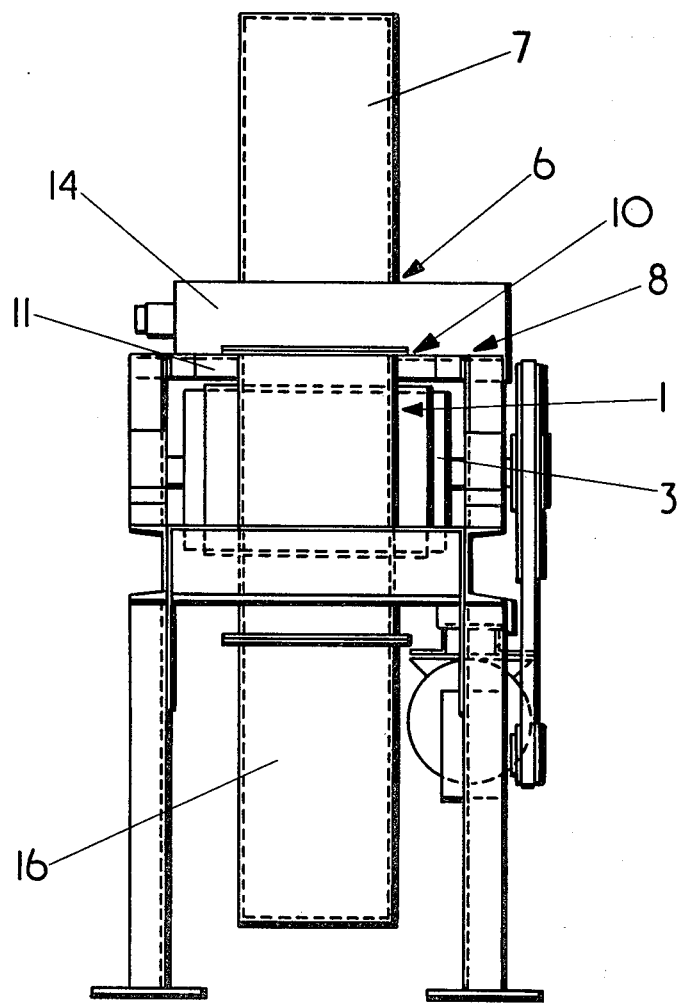
FIG. 2 is a front view of the apparatus of FIG. 1.
Figure 3:
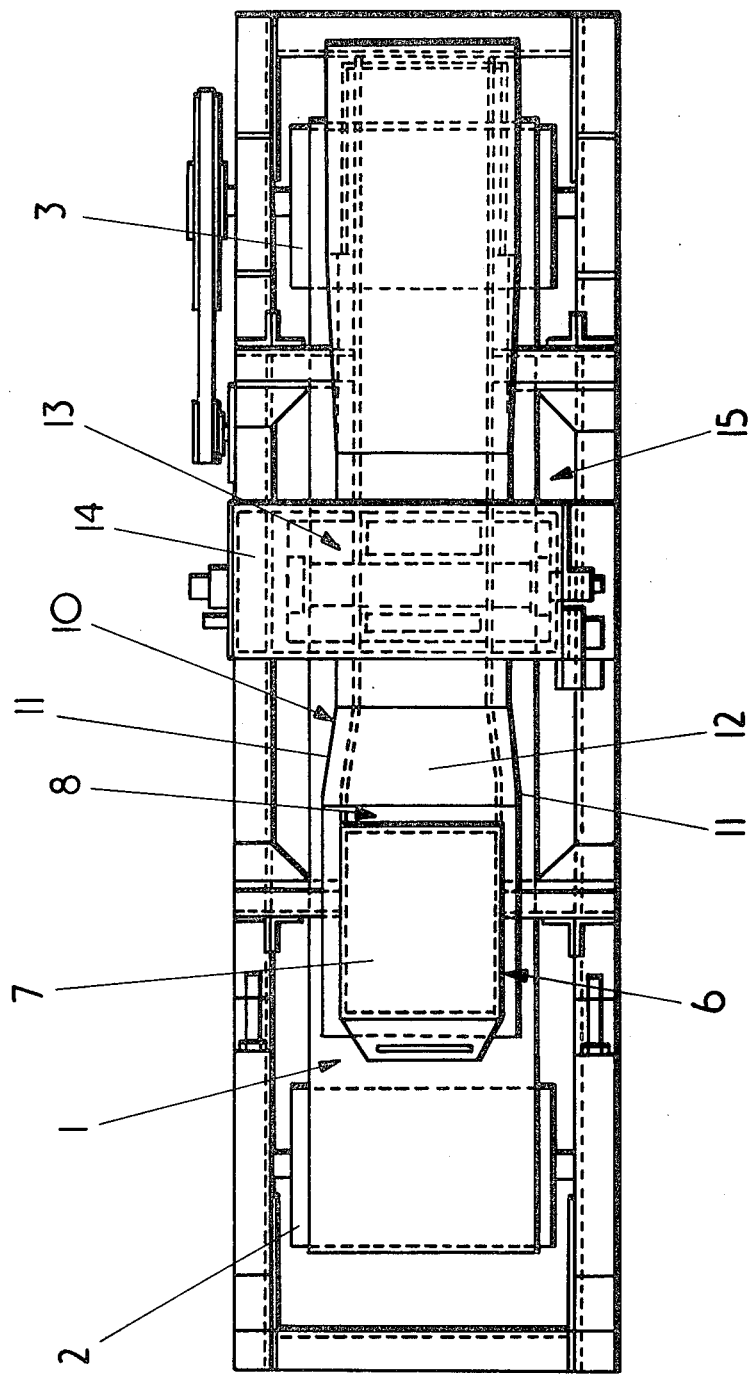
FIG. 3 is a plan of the apparatus of FIG. 1.

Referring to the drawings, the apparatus comprises a linear belt conveyor 1 having a flat conveying surface and passing around two pulleys 2 and 3 one of which is driven by an electric motor 4 mounted beneath the conveyor. A delivery station 6 provided adjacent to the upstream end of the conveyor comprises a feed hopper 7 arranged to deliver material onto the conveying surface of the conveyor, the material being fed to a guide assembly 8 positioned on the downstream side of the delivery station for defining the upper and side boundaries of a bed of material being conveyed by the conveying surface. The guide assembly is constituted by an inverted trough shaped guide extending from the material outlet of the feed hopper.

The bed of material is then compacted by compaction means 10 extending from the guide assembly and forming part thereof and constituted by a reduction in the area of cross-section of the trough shaped guide. The two side walls 11 and the upper wall 12 of the trough shaped guide are inclined to the conveying direction so that the bed of material is compacted as it is conveyed through the compaction means 10.

The compacted bed of material is then conveyed through a sampling section 13 where the material is presented to a beam of electro-magnetic radiation, for example X or gamma radiation for the purpose of determining some characteristic of the material, for example ash content of a coal sample by measuring the amount of radiation back-scattered by the compacted bed of material.

The sampling section includes a source and detector of the radiation and a proportional counter housed within a chamber 14 which interlocks with the support frame 15 so that the source of radiation cannot be removed unless it is first made safe.

The sampled material is then discharged into a collection bin 16 from where it can be discarded or once again fed into the feed hopper to be resampled. Sampling may be repeated several times to enable a mean reading to be obtained.

In use to determine the ash content of a coal sample, the sample is fed into the feed hopper and the sampling equipment switched on. The conveyor 1 is started so that a bed of material is conveyed from the feed hopper outlet into the guide assembly. The bed of material is then passed through the compaction means where the bed is compacted prior to its being presented to the beam of radiation. The bed remains compacted at least until it has passed through the sampling section after which it is discharged into the collection bin.

The amount of back scattered radiation is monitored for the known time that the compacted bed of material is being sampled. Thus, it is possible to deduce the average ash content of the material sampled. By resampling the collected material a mean value of the ash content can be obtained.

From the above description it can be seen that the present invention provides apparatus which enables a rapid determination of the ash content of a coal sample. The apparatus is also simple to operate.

I claim:

1. Apparatus for continuously presenting a uniform bed of finely divided or particulate solid material to a beam of electro-magnetic radiation to determine a characteristic of the material, comprising:
   a linear conveyor having a flat material conveying surface,
   means for driving said conveyor at a substantially continuous and uniform speed,
   a feed hopper positioned adjacent the upstream end of said conveyor for delivering the material onto the moving conveying surface,
   a stationary inverted trough shaped guide assembly extending from beneath the downstream side of said feed hopper with its longitudinal axis substantially parallel to the conveyor and having a first zone with substantially parallel walls for defining the upper and side boundaries of the bed of material being conveyed and a second zone with all walls inclined toward the conveying direction to provide compaction of the material passing therethrough so that the bed of material is of a substantially constant bulk density,
   a sampling section having a source and detector of electro-magnetic radiation positioned adjacent said guide assembly in which the bed of material is presented to a beam of electro-magnetic radiation for determining a characteristic of said material, and a collection means positioned adjacent the downstream end of said conveyor into which the sampled material is discharged and collected.

2. An apparatus as claimed in claim 1, in which the electro-magnetic radiation comprises χ or gamma radiation and the particulate material is coal in which the ash content thereof is determined.

3. An apparatus as claimed in claim 1, in which the guide assembly is positioned substantially adjacent and above said conveyor.

4. Apparatus for continuously presenting a uniform bed of substantially constant bulk density, finely divided or particulate solid material to a beam of electromagnetic radiation to determine a characteristic of the material, comprising:

a linear conveyor having a flat material conveying surface, a motor means for driving said conveyor at a substantially continuous and uniform speed, a feed hopper positioned adjacent the upstream end of said conveyor for delivering the material onto the moving conveyor surface, a stationary trough shaped guide assembly adjacent and extending from beneath the downstream side of said feed hopper and having a first zone with substantially parallel walls for defining the upper and side boundaries of the bed of material being conveyed and a second zone with all walls inclined toward the conveying direction to provide compaction of the material passing therethrough so that the bed of material is of a substantially constant bulk density, a sampling section positioned adjacent said guide assembly in which the bed of material is presented to a beam of electro-magnetic radiation for determining a characteristic of said material, and a collection means positioned adjacent the downstream end of said conveyor into which the sampled material is discharged and collected.

5. An apparatus as claimed in claim 4, in which the electro-magnetic radiation comprises χ or gamma radiation and the particulate material is coal in which the ash content thereof is determined.

6. An apparatus as claimed in claim 4, in which the guide assembly is positioned substantially adjacent and above said conveyor.

7. Apparatus for continuously presenting a uniform bed of substantially constant bulk density, finely divided or particulate solid material to a beam of electromagnetic radiation to determine a characteristic of the material, comprising:

a linear conveyor having a flat material conveying surface, motor means for driving said conveyor at a substantially continuous and uniform speed, a feed hopper positioned adjacent to the upstream end of said conveyor for delivering material onto the moving conveyor surface, a stationary inverted trough shaped guide assembly extending from the downstream side of said feed hopper and having a first zone in which the walls of the inverted trough define the upper and side boundaries of the bed of material being conveyed, a second zone on the downstream side of the first zone, in which all walls of the inverted trough are inclined to define a reducing area of cross section in the conveying direction such that in use material in the bed is compacted as a result of the reducing area of cross section as it is conveyed through such guide assembly, and a third zone on the downstream side of the second zone, in which the bed of material is maintained compacted and in which the compacted bed is presented to the beam of electro-magnetic radiation to determine a characteristic of the material, a sampling section associated with said third zone of the guide assembly and having a source and detector of electro-magnetic radiation for emitting and sensing the beam, respectively, and collection means positioned adjacent to the downstream end of said linear conveyor into which the sampled material is discharged.

* * * * *